United States Patent [19]

Winsor

[11] Patent Number: 5,309,496

[45] Date of Patent: May 3, 1994

[54] FILMLESS X-RAY APPARATUS AND METHOD OF USING THE SAME

[76] Inventor: Robin W. Winsor, 1439 Lake Twintree Way SE, Calgary, Alberta, Canada, T2J 2X6

[21] Appl. No.: 995,966

[22] Filed: Dec. 23, 1992

[51] Int. Cl.$^5$ .............................................. H05G 1/64
[52] U.S. Cl. .................................... 378/98.2; 378/62
[58] Field of Search ............................ 378/62, 98, 99; 358/111

[56] References Cited

U.S. PATENT DOCUMENTS

| 3,860,817 | 1/1975 | Carmean . | |
|---|---|---|---|
| 4,412,346 | 10/1983 | Takenouti et al. . | |
| 4,761,805 | 8/1988 | Sebring . | |
| 4,821,727 | 4/1989 | Levene et al. | 378/37 |
| 4,890,313 | 12/1989 | Lam et al. | 378/65 |
| 4,924,487 | 5/1990 | Nishiki . | |
| 4,979,198 | 12/1990 | Malcolm et al. . | |
| 4,995,068 | 2/1991 | Chou et al. . | |
| 5,090,042 | 2/1992 | Bejjani et al. | 378/99 |
| 5,211,165 | 5/1993 | Dumoulin et al. | 378/62 |

Primary Examiner—David P. Porta
Attorney, Agent, or Firm—Jerry T. Kearns

[57] ABSTRACT

A filmless X-ray apparatus and method of using the same include an X-ray source for directing X-rays through a subject such as an animal, human, or luggage in an airport security scanner into a fluorescent intensifying screen. An aluminum coated and lead back glass mirror reflect only the visible component of radiation passing through the fluorescent screen to one or more video cameras. Video signals from the video camera are directed to frame grabber circuitry operably associated with a computer provided with image enhancing and processing software.

25 Claims, 2 Drawing Sheets

FILMLESS X-RAY APPARATUS AND METHOD OF USING THE SAME

BACKGROUND OF THE INVENTION

1. Field of the Invention

The present invention is directed to apparatus for the direct detection and computer enhancement of X-rays which obviates the need for X-ray film, developers, fixers, and processing equipment associated with prior art X-ray methods. The inventive apparatus provides faster image processing than conventional methods and requires less exposure for the subject. The inventive method and apparatus has advantages over the new computed radiography techniques including simplicity and potential for low cost application. This X-ray method and apparatus of the present invention has applications in many fields including airport security systems, industrial quality control, and medicine.

2. Description of the Prior Art

For almost eighty years photographic films have been used both to capture and display X-rays for diagnostic purposes. (See FIG. 1). Only in the last ten years have any alternative methods of X-ray imaging started to appear. Best known of these is the expensive and complicated CAT scan system used in many hospitals. Less well known filmless X-ray systems are now available which use a storage phosphor device to capture the X-ray image. These so called image plates can be scanned by a laser bean a short time later, causing the image plates to emit light proportional to the intensity of X-rays to which they were previously exposed. Such systems are also complicated and expensive, requiring special laser equipment for the scanning stage. They have however clearly demonstrated the great advantages of filmless, or digital, X-ray pictures.

Digital recorded X-rays are superior to those recorded with photographic film due to the greater dynamic range of the digital recording system. Photographic methods allow approximately one order of magnitude dynamic range whereas digital methods typically allow four orders of magnitude. This advantage is only realized if the actual capture of the X-ray image is digital. Merely scanning a previously recorded photographic X-ray will not do. In addition to the inherent advantages of the increased dynamic range, computer image processing techniques provide a wealth of capabilities to study otherwise obscured details within the image. Accordingly, the present invention proposes a filmless X-ray apparatus and method of using the same which has all the advantages of digitally captured radiography and in addition is mechanically very simple. This allows the apparatus to be made at much lower cost than current systems, making it suitable for installation in many more locations, e.g. radiology clinics outside of hospitals, veterinary clinics, chiropractic clinics, etc. The inventive apparatus will be a particular boon to remote settlements where "tele-medicine" is practiced, such as northern Canada and Alaska, because it allows an X-ray image signal to be transmitted over phone lines without an unacceptable loss of resolution.

SUMMARY OF THE INVENTION

In the instant apparatus, X-rays are passed from a conventional X-ray source through a subject (patient) in the usual manner. In most conventional X-ray methods, the film is mounted in a cassette between two layers of fluorescent material. When the X-rays strike the fluorescent material, visible light is produced. This enhances the photographic effect on the X-ray film. (See U.S. Pat. Nos. 2,298,587 and 2,161,058, for example). In the present invention, employs no film and only one fluorescent layer. A mirror mounted below the fluorescent layer at 45 degrees to the path of the X-ray beam allows the X-rays to pass through the mirror with their path unaltered, but reflects the brief visible light image created by the passage of X-rays through the fluorescent layer on a 90 degree path to the X-ray beam, separating the visible light from the X-rays. This separation is important, because X-rays will destroy most electronic detectors. The 45 degree alignment of the mirror provides an equal path length from the image plane (i.e. the fluorescent screen) to the detector plane regardless of the position on the image plane, thus ensuring that a part of the image formed on the left of the fluorescent screen will be sharply in focus at the same time as a part from the right side. To minimize scattered radiation, the mirror possesses an aluminum reflective layer on the front, rather than the conventional silver backing, because aluminum is relatively transparent to X-rays. Behind the reflective aluminum layer and glass substrate, the mirror is coated with lead to absorb X-rays. A CID (Charge Injection Device) detector, in the form of a video camera disposed at the end of the 90 degree visible light path registers the image. The CID video camera is used rather than the generally available CCD cameras because multiple frames may be stacked with a CID video camera. CCD cameras destroy the captured image while reading it out and so do not allow for image stacking. Without the CID, camera light levels may fall below the usable threshold. While the use of a CID camera is preferred in this device, a CCD camera of sufficient sensitivity could also be used. A photocell detector near the fluorescent screen registers the burst of visible light and initiates capture of the image on the video camera by a frame grabber. A frame grabber is essentially a circuit board mounted inside a computer which translates a video image into a standard computer graphics file format such as TIFF (Tagged Image File Format) for analysis and enhancement by the computer. This board may be one of any number of commercially available products and will incorporate image processing software as well as its ability to capture the image. The use of the photocell coordinated frame grabber obviates the need for more expensive techniques now being introduced in the field of computed radiography such as storage phosphors combined with laser scanning.

The whole apparatus, except for the computer, is enclosed in a light proof, lead lined box. The height of the box is determined by the size of the fluorescent screen, as the mirror mounted beneath the fluorescent screen must be of the same size. For example, an 8 inch by 10 inch screen requires a like sized mirror. With the mirror mounted at 45 degrees, the box height is the square root of 32 or approximately 5.65 inches. The length of the box is determined by the focal length of the camera in use. In one example embodiment, a box length of approximately 3 feet is utilized.

Experiments have shown that the image is captured in the time taken to register a single frame of video, typically 1/60 of a second. As photographic methods in radiology normally require exposures of 1/10 to 1 second, the method of the present invention allows for either a multiplicity of images to be captured in the same time period or for the radiation exposure to be greatly reduced. If the multiplicity of images is used, they may then be stacked together. The signal, or desirable part of the picture, will be increased by the number of pictures stacked. Any random noise however will increase only by the square root of the number of pictures stacked. This yields a signal to noise ratio improvement multiplier equal to the square root of the number of pictures stacked. If, for example, four pictures of the same subject are stacked together, the signal to noise ratio will improve by a factor of two.

In current methods, an effect known as "heeling" causes a variation of intensity from one end of the X-ray image to the other due to the angle at which the X-rays are emitted from the focal spot of the X-ray machine. This heeling effect must be allowed for in examining X-ray films. In the inventive method, the heeling effect may be electronically processed out at the image enhancement stage.

If a subject (patient) moves during exposure, as is common in veterinary medicine, the radiograph is useless for diagnostic purposes using current methods. In the method of the present invention, image processing software allows for the removal of blur caused by linear motion. A computer image can therefore be corrected, rather than repeating the exposure. This saves time and reduces patient exposure in medical applications. When used in an airport security scanner, the inventive X-ray apparatus allows continuous operation without having to pause for each picture, especially as the rate of motion causing the blur would be a known constant determined by the speed of conveyor belt movement.

While an image obtained with a single video camera may be adequate for most purposes, inevitably some applications will require a higher resolution. To this end, a second embodiment of the invention uses not one, but many video cameras. As suitable video cameras are commercially available which measure only one or two inches in size, it is feasible to mount as many as are required along a back plane of a light proof box housing the imaging apparatus. The desired resolution may then be obtained by forming a composite of all the captured images, each of which will have the same detailed spatial resolution.

These and various other advantages and features of novelty which characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described preferred embodiments of the invention.

DETAILED DESCRIPTION OF THE PREFERRED EMBODIMENT(S)

Figure 1:
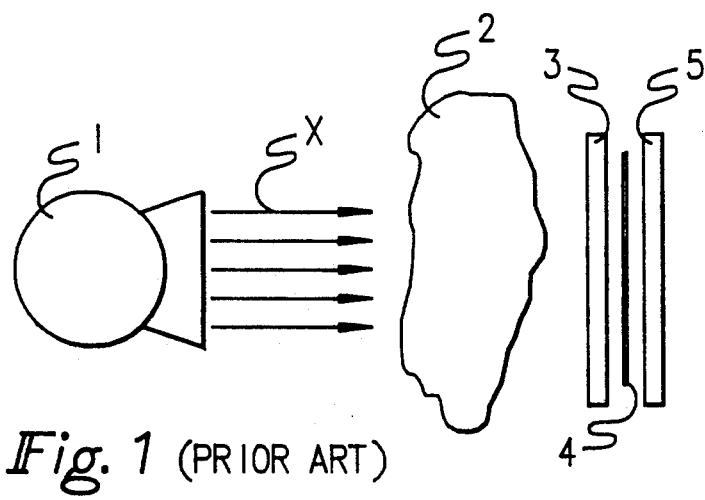
FIG. 1 is a block diagram illustrating prior art film type X-ray apparatus.

As shown in FIG. 1, a prior art film type X-ray apparatus typically includes an X-ray source 1, which directs X-rays X toward and through a subject 2, for example a human, animal, or luggage at an airport security device. The X-rays subsequently pass through a fluorescent intensifying screen 3, for the purpose of producing light radiation in the spectrum which can be recorded on a photographic film plate 4. The photographic film 4 is typically sandwiched between a first fluorescent intensifying screen 3 and a second fluorescent intensifying screen 5 which includes a lead backing for preventing the harmful emission of X-ray radiation.

Figure 2:
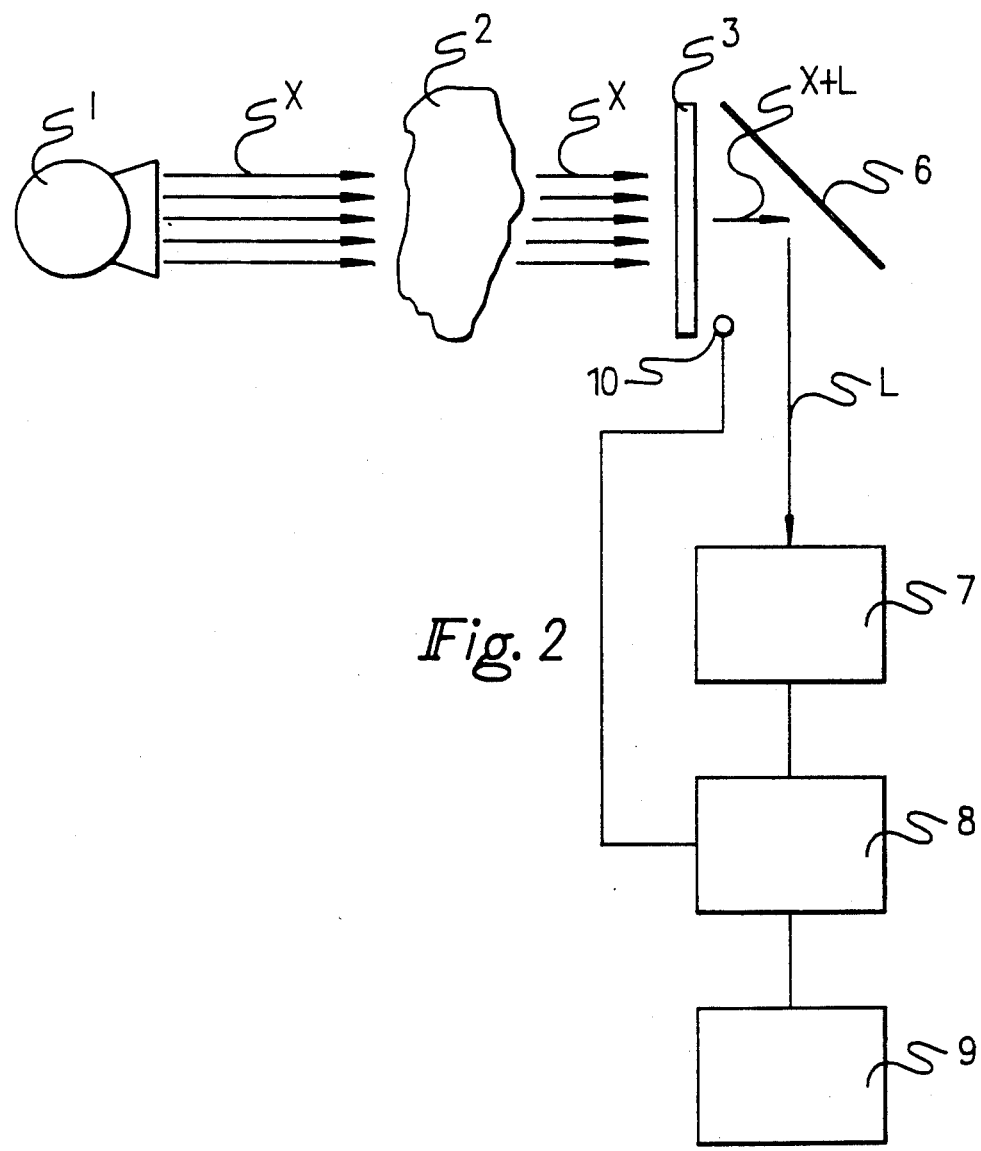
FIG. 2 is a block diagram diagrammatically illustrating a filmless X-ray apparatus according to a first embodiment of the present invention.
Figure 4:
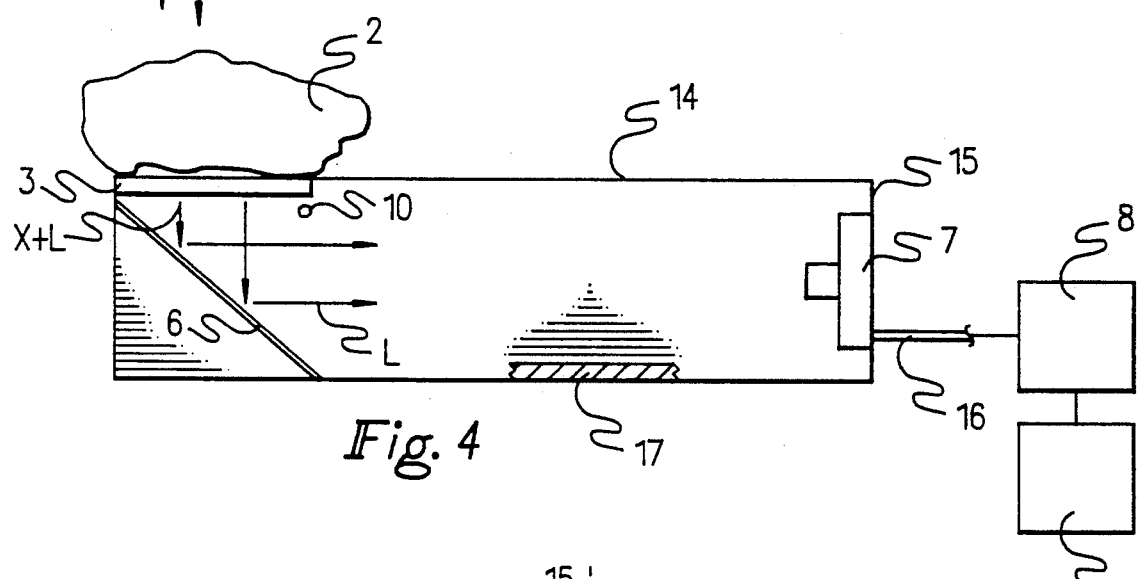
FIG. 4 is a diagrammatic side elevational view illustrating the housing, fluorescent screen, mirror and video camera components of the filmless X-ray apparatus of the present invention.

According to a first embodiment of the present invention, illustrated in FIGS. 2 and 4, a conventional X-ray source 1 emits X-rays X toward and through a subject 2. The X rays travel through the subject 2 and a conventional fluorescent intensifying screen 3. One suitable type of fluorescent intensifying screen is sold under the designation DUPONT CRONEX QUANTA III (TM) and distributed by Medtec Marketing Ltd, of Calgary, Alberta, Canada and many other sources. As a result of passage through fluorescent screen 3, X-rays and a visible component of the light spectrum, indicated by the arrows designated X+L, impinge upon a mirror 6 disposed at a 45 degree included angle relative to the plane of the screen 3.

Figure 3:
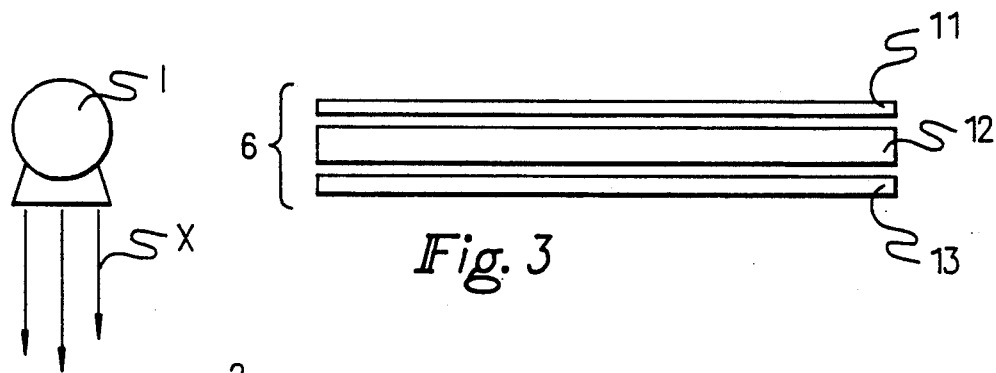
FIG. 3 is an exploded side elevational view of a mirror component of the filmless X-ray apparatus of the present invention.

As shown in FIG. 3, the preferred mirror 6 for use in the present invention comprises a front surface coated by an aluminum "silvering" layer 11 on a glass substrate 12 provided with a lead backing layer 13.

After being reflected by the mirror 6, the visible component of radiation L is directed toward a CID video camera. One suitable conventional form of CID video camera for use in the present invention is available from CIDTEC of Liverpool, New York, U.S.A. under the designation CIDTEC model no. CID3710D solid state monochrome video camera. The X-ray component of the radiation is not reflected by the mirror 6, but is rather absorbed by the lead backing 13 of the mirror 6 (FIG. 3), or by a lead lining 17 within a light tight housing 14. The video signal produced by the video camera 7 is directed by a conventional video coaxial cable 16 or other suitable connector to a frame grabber circuit 8 operably connected to a computer 9, for example an IBM compatible PC type computer. One example commercially available frame grabber circuit is available from DataCube of Peabody, Mass., U.S.A., under the designation DataCube QVC-423 associated suitable image processing software is available from Sun Microsystems of Mountain View, Calif., U.S.A. under the designation SunVision. Alternative example image processing software is available under the designation Aldus PhotoStyler (TM) in most retail computer software stores.

In order to initiate and control the frame grabber to capture an image from the video camera 7, a photocell 10 is positioned behind the fluorescent intensifying screen 3 and is operably connected to activate the frame grabber 8 upon emission of visible spectrum light from the screen 3 which impinges upon the photocell 10. Suitable conventional control circuits may be utilized in association with the frame grabber 8 to control the capture of single or multiple images from the video camera 7 disposed on the back plane 15 of the housing 14.

Figure 5:
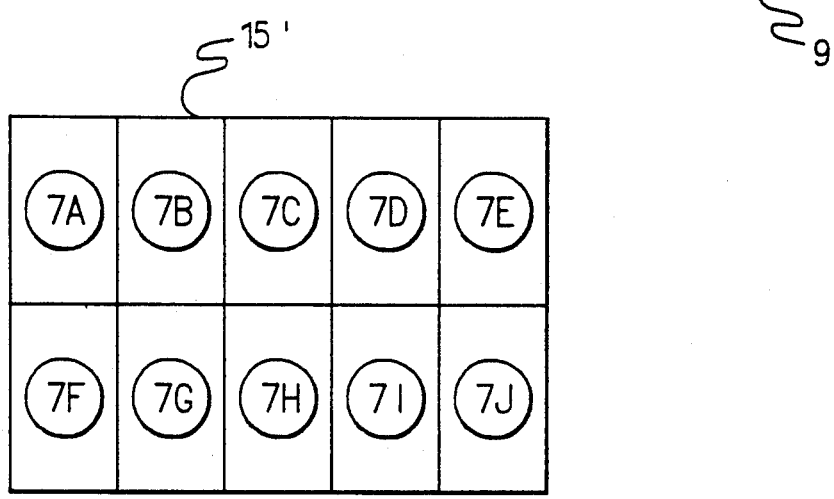
FIG. 5 is a block diagram depicting a back plane of a light proof box component of a filmless X-ray apparatus according to a second embodiment of the invention.

FIG. 5 illustrates a modified back plane 15, according to a second embodiment of the present invention, in which a plurality of video cameras 7A, 7B, 7C, 7D, 7E, 7F, 7G, 7H, 7I, and 7J are mounted for the purpose of capturing multiple images to achieve enhanced resolution.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A filmless X-ray apparatus, comprising:
   an X-ray source disposed for directing X-rays through a subject;
   a fluorescent intensifying screen mounted at least partially in the path of the X-rays passing through the subject;
   a mirror disposed at an oblique angle behind said fluorescent intensifying screen;
   a video camera oriented at an oblique angle relative to said mirror so as to receive only a visible component of reflected radiation from said mirror;
   a frame grabber operably connected for receiving a video signal from said video camera;
   a computer operably associated with said frame grabbler for processing and enhancing an image received by said video camera; and
   a photocell disposed for receiving radiation visible spectrum from said fluorescent intensifying screen and operably associated for controlling capture of images from said video camera by said frame grabber.

2. The filmless X-ray apparatus of claim 1, further comprising a plurality of video cameras operably disposed for receiving visible spectrum light radiation reflected from said mirror.

3. The filmless X-ray apparatus of claim 1, wherein said mirror is disposed at a 45 degree angle with respect to a plane of said fluorescent intensifying screen.

4. The filmless X-ray apparatus of claim 1, wherein said computer and frame grabber include image enhancing and processing software.

5. The filmless X-ray apparatus of claim 1, wherein said mirror is coated with aluminum.

6. The filmless X-ray apparatus of claim 1, wherein said mirror includes a lead backing.

7. The filmless X-ray apparatus of claim 1, wherein said fluorescent intensifying screen, said mirror, and said video camera are each at least partially mounted within a lead lined light proof housing.

8. A filmless X-ray apparatus, comprising:
   an X-ray source disposed for directing X-rays through a subject;
   a fluorescent intensifying screen mounted at least partially in the path of the X-rays passing through the subject;
   a mirror disposed at an oblique angle behind said fluorescent intensifying screen;
   a plurality of video cameras operably disposed for receiving only a visible component of radiation reflected from said mirror;
   a frame grabber operably connected for receiving a video signal from said video camera; and
   a computer operably associated with said frame grabber for processing and enhancing an image received by said video camera.

9. The filmless X-ray apparatus of claim 8, wherein said mirror is disposed at a 45 degree angle with respect to a plane of said fluorescent intensifying screen.

10. The filmless X-ray apparatus of claim 8, wherein said computer and frame grabber include image enhancing and processing software.

11. The filmless X-ray apparatus of claim 8, wherein said mirror is coated with aluminum.

12. The filmless X-ray apparatus of claim 8, wherein said mirror includes a lead backing.

13. The filmless X-ray apparatus of claim 8, wherein said fluorescent intensifying screen, said mirror, and said video camera are each at least partially mounted within a lead lined light proof housing.

14. A filmless X-ray method, comprising the steps of:
   providing an X-ray source and directing X-rays from said source through a subject;
   providing a fluorescent intensifying screen mounted at least partially in the path of the X-rays passing through the subject to produce light radiation in the visible spectrum;
   providing a mirror disposed at an oblique angle behind said fluorescent intensifying screen and reflecting said light in the visible spectrum;
   providing a video camera oriented at an oblique angle relative to said mirror and receive said visible light component of reflected radiation from said mirror;
   providing a frame grabber and receiving and capturing with said frame grabber a video signal from said video camera;
   providing a computer operably associated with said frame grabber and processing and enhancing an image received by said video camera; and
   providing a photocell disposed for receiving radiation in the visible spectrum from said fluorescent intensifying screen and controlling capture of images from said video camera by said frame grabber dependent upon a signal transmitted from said photocell.

15. The method of claim 14, further comprising the step of providing a plurality of video cameras and receiving visible spectrum light radiation reflected from said mirror by each of said video camera.

16. The method of claim 14, wherein said mirror is disposed at a 45 degree angle with respect to a plane of said fluorescent intensifying screen.

17. The method of claim 14, wherein said computer and frame grabber include image enhancing and processing software.

18. The method of claim 14, wherein said mirror is coated with aluminum.

19. The method of claim 14, wherein said mirror includes a lead backing.

20. The method of claim 14, wherein said fluorescent intensifying screen, said mirror, and said video camera are each at least partially mounted within a lead lined light proof housing.

21. A filmless X-ray method, comprising the steps of:
   directing X-rays from an X-ray source through a subject;

producing light in the visible spectrum proportional to the intensity of X-rays passing through the subject;

reflecting said light in the visible spectrum at an oblique angle;

reflecting said visible light component of reflected radiation with a digital receiving device;

capturing a video signal from said digital receiving device;

computer processing and enhancing an image represented by said captured video signal; and controlling capture of video signals from said digital receiving device dependent upon a first incidence of said light in the visible spectrum.

22. The method of claim 21, further comprising the step of substantially simultaneously receiving and capturing a plurality of video signals from a plurality of digital receiving devices.

23. A filmless X-ray method, comprising the steps of:

directing X-rays from an X-ray source through a subject;

producing light in the visible spectrum proportional to the intensity of X-rays passing through the subject;

reflecting said light in the visible spectrum at an oblique angle;

substantially simultaneously receiving said visible light component of reflected radiation with a plurality of digital receiving devices and capturing a plurality of video signals from said plurality of digital receiving devices; and computer processing and enhancing an image represented by said captured video signal.

24. A filmless X-ray apparatus, comprising:

means for providing a source of X-rays disposed for directing X-rays through a subject;

means for producing light in the visible spectrum proportional to the intensity of X-rays passing through a subject and disposed at least partially in the path of the X-rays passing through the subject;

means for reflecting light in the visible spectrum disposed for reflecting light produced by said means for producing light in the visible spectrum;

means for producing a video signal representation of said produced light in the visible spectrum disposed for receiving light reflected by said means for reflecting light;

means for capturing a video signal operably connected for receiving a video signal from said means for producing a video signal;

processing means operably associated with said means for capturing a video signal for processing and enhancing an image received by said means for producing a video signal; and means for receiving radiation and operably associated for controlling capture of images from said means for producing a video signal by said means for capturing a video signal.

25. A filmless X-ray apparatus, comprising:

means for providing a source of X-rays disposed for directing X-rays through a subject;

means for producing light in the visible spectrum proportional to the intensity of X-rays passing through a subject and disposed at least partially in the path of the X-rays passing through the subject;

means for reflecting light in the visible spectrum disposed for reflecting light produced by said means for producing light in the visible spectrum;

a plurality of means each for producing a video signal representative of said produced light in the visible spectrum disposed for receiving light reflected by said means for reflecting light;

means for capturing a video signal operably connected for receiving a video signal from said plurality of means for producing a video signal; and processing means operably associated with said means for capturing a video signal for processing and enhancing an image received by said means for producing a video signal.

* * * * *

UNITED STATES PATENT AND TRADEMARK OFFICE
CERTIFICATE OF CORRECTION

PATENT NO.   : 5,309,496
DATED        : May 3, 1994
INVENTOR(S)  : Robin W. Winsor It is certified that error appears in the above-identified patent and that said Letters Patent is hereby corrected as shown below:

Column 7,
Line 6, delete "reflecting" and insert -- receiving --.

Signed and Sealed this

Twentieth Day of December, 2005

JON W. DUDAS
*Director of the United States Patent and Trademark Office*